United States Patent [19]

May

[11] Patent Number: 5,089,232

[45] Date of Patent: Feb. 18, 1992

[54] APPARATUS FOR MEASURING THE CONCENTRATION OF GASEOUS AND/OR VAPOROUS COMPONENTS OF A GAS MIXTURE

[75] Inventor: Wolfgang May, Reinfeld, Fed. Rep. of Germany

[73] Assignee: Drägerwerk Aktiengesellschaft, Lübeck, Fed. Rep. of Germany

[21] Appl. No.: 469,394

[22] Filed: Jan. 24, 1990

[30] Foreign Application Priority Data

Jan. 27, 1989 [DE]  Fed. Rep. of Germany ....... 3902402

[51] Int. Cl.$^5$ .................... G01N 21/00; G01N 31/22; G01N 1/48
[52] U.S. Cl. .......................... 422/83; 422/63; 422/57; 422/58; 422/82.05; 422/86; 422/88; 422/93; 436/167
[58] Field of Search ............... 422/83, 86, 93, 99, 422/88, 58, 91, 98, 63, 82.05, 55, 57, 58; 436/151, 165, 169, 902, 167, 57; 235/462, 465

[56] References Cited

U.S. PATENT DOCUMENTS

| Re. 29,725 | 8/1978 | Johnson et al. | 436/165 |
|---|---|---|---|
| 3,924,219 | 12/1975 | Braun | 422/83 |
| 3,985,017 | 10/1976 | Goldsmith | 422/83 |
| 4,235,097 | 11/1980 | Kring et al. | 422/88 |
| 4,269,804 | 5/1981 | Kring | 422/86 |
| 4,678,894 | 7/1987 | Shafer | 235/462 |
| 4,935,875 | 6/1990 | Shah et al. | 235/462 |
| 4,963,324 | 10/1990 | May | 422/60 |

FOREIGN PATENT DOCUMENTS

| 1037725 | 2/1959 | Fed. Rep. of Germany . |
| 1598021 | 3/1970 | Fed. Rep. of Germany . |
| 2628790 | 7/1978 | Fed. Rep. of Germany . |
| 2626600 | 7/1979 | Fed. Rep. of Germany . |

OTHER PUBLICATIONS

Grace Company, Grundlagen-Einführung.
Grace Company, Grundlagen-Aufbau+Struktur.

Primary Examiner—Robert J. Warden
Assistant Examiner—Theresa A. Trembley
Attorney, Agent, or Firm—Walter Ottesen

[57] ABSTRACT

The invention is directed to an arrangement for measuring the concentration of gaseous or vaporous components of a gas mixture by using optically distinguishable reaction zones from gas test tubes which contain a substance reacting with the component to be detected. The change of the reaction zone is determined by means of direct observation and/or by means of an opto-electronic scanning device. This arrangement is improved in accordance with the invention in that the reacting substance is accommodated at least in one channel formed in a carrier. The channel has a cross section in the reaction zone which is less than 1 mm$^2$.

23 Claims, 3 Drawing Sheets

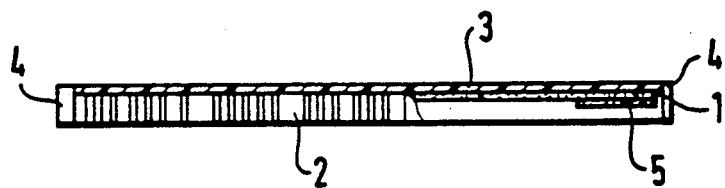
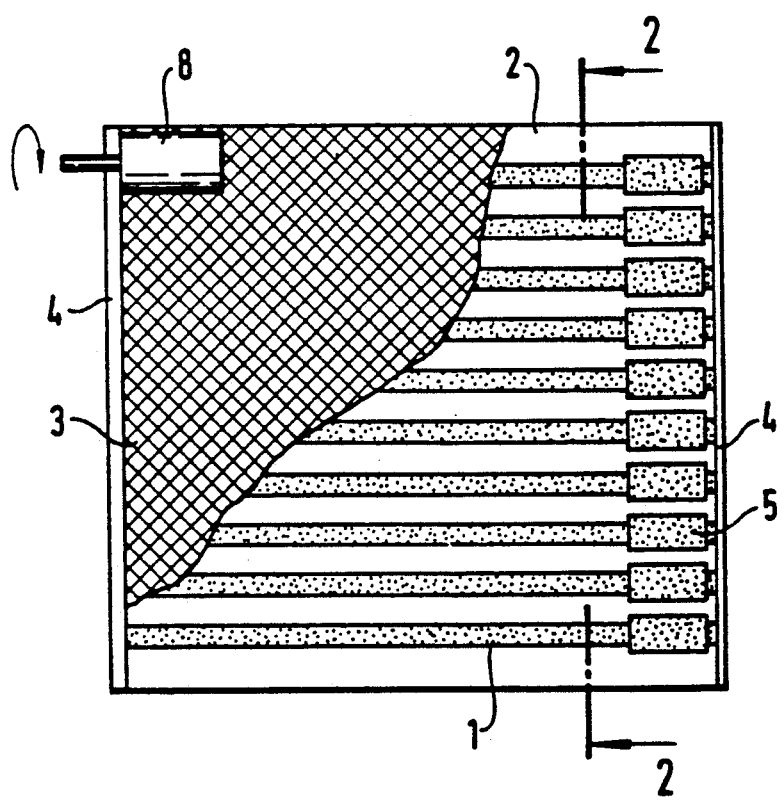
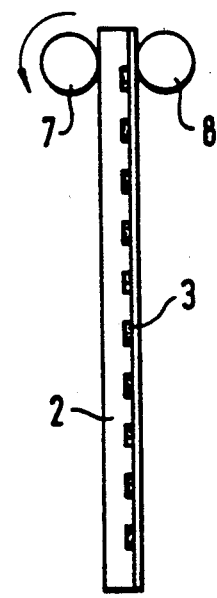

APPARATUS FOR MEASURING THE CONCENTRATION OF GASEOUS AND/OR VAPOROUS COMPONENTS OF A GAS MIXTURE

FIELD OF THE INVENTION

The invention relates to an apparatus for measuring the concentration of gaseous and/or vaporous components of a gaseous mixture by utilizing optically distinguishable reaction zones of gas testing tubes which contain a substance reacting with the component to be detected with the change of the reaction zone being determined by a direct observation and/or by means of an opto-electronic scanning device.

BACKGROUND OF THE INVENTION

Gas testing tubes are used in a known manner for measuring the concentration of dangerous substances at a workplace and the spectrum of the gases and vapors to be determined is known and thereby the selection of corresponding measuring tubes based on earlier measurements of the occurring substances is known.

Certain difficulties occur when contaminants of an unknown type and concentration are to be detected without a complex precise determination of contaminants by means of laboratory measurements. The contaminants can, for example, occur at a special waste disposal facility or as a consequence of a chemical accident. In these applications, test tubes in a combined arrangement offer substantial time advantages when determining contaminants and the information which they provide can be used for evacuation measures which have to be rapidly initiated or the information provided can be used to exclude the possibility of evacuation because a corresponding danger is not present.

In such measuring devices, there are mostly several and sometimes up to twenty different test tubes which must be charged with the mixture to be investigated. For this reason and because the measuring results of the individual test tubes must be made available quickly and simultaneously and, if required, for further processing in an electronic evaluation apparatus, the problem is presented that an arrangement must be used having a high sensitivity for the individual test tubes. Furthermore, such an arrangement should afford the possibility of a rapid exchange of the test tubes in their entirety.

German Patent 26 26 600 discloses a measuring apparatus wherein several test zones are sequentially scanned by a common opto-electronic scanning device with selective illuminating and transmitting elements in the time-division-multiplex method. Such test strips having several reaction zones separated from one another are used for investigating liquids such as for medical urine tests.

SUMMARY OF THE INVENTION

It is an object of the invention to improve on the known principle of using test tubes for investigating a gaseous and/or vaporous mixture so that a plurality of test reactions as may be required can be carried out with a relatively minimal use of reagents with high response sensitivity in a compact space-saving arrangement.

According to a feature of the invention, the reacting substance is accommodated in at least one channel formed in a carrier with the channel having a cross section in the reaction zone which is less than 1 mm$^2$. A channel formed in this manner has essentially the character of a test tube and provides a capability of detecting the corresponding contaminant with high sensitivity and a low quantity of detecting substance. The contaminant can be detected in concentrations which for test tubes having conventional dimensions would permit no distinguishable coloration zone. The low amount of detecting substance causes a relatively low effect on the environment because of the carrier which is configured preferably as a throw-away article and has channels arranged thereon. Furthermore, only a few ml/min of a through-suction volume per channel is required for such micro testing tubes in the form of channels. This means very small pumps and low power battery operation.

The channels can be arranged on the carrier in the most various geometric configurations and can have a spiral or zigzag form with each channel containing the same detecting substance or containing several different detecting substances. Throughflow as well as diffusion testing tubes can thereby be simulated. In the case of diffusion test tubes, it is not necessary to provide a quieting segment upstream for obtaining an undisturbed diffusion because of the small channel cross section. The throttling effect of the channel caused by the small cross section replaces an additional throttle, which limits the flow speed, for through-flow test tubes.

According to an advantageous embodiment of the invention, the cross section of the channel or of the channels of a multiple arrangement is below 10 $\mu$m$^2$. A plurality of parallelly connected channels or separately connectable channels can be arranged on the carrier with a single channel or the plurality of channels being extended to define a linear or curved path.

A quieted diffusion in the channel is provided from the entrance of the gas specimen into the channel so that a separate quieting counter segment arranged upstream or a flow throttle is unnecessary. Notwithstanding the high throttling effect of the channel, a coloration zone which advances with adequate rapidity is provided so that the evaluation of the detection zone by means of rapid optical evaluation units is meaningful. A channel configured in these dimensions makes possible a highly sensitive detection of the substance to be detected notwithstanding the advantageously low indicator quantities. The low quantity of indicator substance in comparison to known test tubes having indicator charges up to several cubic centimeters brings with it a significantly lower cost to the environment with respect to used test tubes.

According to an advantageous embodiment, the channel or the channels can be etched into a plate-like carrier. Another advantageous production possibility is afforded by compression molding the channels in a plate-like carrier. The channel can also be advantageously ground on a plate-like carrier. The plate-like carrier can preferably be made of glass or ceramic but it also can be made of plastic or metal. Basically, all production methods are suitable by means of which recesses defining a line path can be produced having a shallow depth in metal or nonmetal materials.

According to another embodiment of the invention, the channel can be configured so as to lie between a plate-shaped carrier and a surface coating. Another possibility provides for forming the channel arrangement between the plate-shaped carrier and a cover plate which is preferably made of the same material. The individual channels can be configured in various ways as in test tubes with the known additional configuration with forward layer, blockage and the like.

The channels are coated with the indicator or with the reagent. The reduced expansion requires that silica gel be applied either to the base of the channel or to the channel surfaces facing the evaluation unit by means of an inert adhesive. The silica gel is applied to indicator carriers in the form of small beads coated with the indicator.

Because of the reduced spatial dimensions, it is advantageous to arrange several channels on a chip-shaped carrier exchangeably inserted into an opto-electronic scanning device. The opto-electronic scanning device can be configured, for example, as disclosed in published German patent application DE-OS 15 98 021 or German Patent 26 28 790. The opto-electronic scanning device can be configured for all or several channels or an individual channel.

According to another embodiment, several channels can be connected to an opto-electronic scanning device or they can be brought sequentially into the measuring range of this scanning device and the output signals determined from scanning the individual channels can be fed to a microprocessor for evaluation. In this connection, only threshold values such as color saturation and/or the location of the coloration length can be evaluated as digital measurement variables. A threshold value determination for a coloration saturation has as a condition precedent that also color saturation measurements in contrast to coloration length measurements can be carried out with such micro test tubes. Actually, these channel arrangements are suitable for coloration length measurements as well as for color saturation measurements when appropriate opto-electronic scanning devices are used which are already known. The digital patterns of the channels arising in this manner receive via a ROM-table the assignment to the list of participating substance groups and deliver, as required, also indications for further measurements. The output signals determined by scanning the individual channels and fed into the microprocessor can be analyzed by means of a stored plausibility model for gaseous or vaporous mixtures of unknown compositions so that at least an indication to the type of contaminant present can be provided.

In so-called arrays, multiple arrangements of channels are assembled in correspondence to individual test tubes with which also non-specific channels, for example for acids, as in similar known multipurpose test tubes can be included. A special contaminant causes a certain combination of channels from the array to respond and the indicators are supplied to the microprocessor. The microprocessor then names the suspected contaminants or contaminant groups as required with the aid of the plausibility model.

A hermetic closure of the channel or channels until their use can be provided in the same manner as for gas test tubes. For this purpose, breakable points or end openings closed with foil can be used which can be pulled off or perforated.

For producing such measurement apparatus with channels for ammonia or hydrochloric acid, the smallest glass beads having a diameter of several micrometers or less are mixed in a dry condition with bromocresol green and glued to plastic carriers which serve to later coat the channels after suitable machining (for example, cutting). The bromocresol green is fixed as an indicator on the surface of the beads according to the sol-gel-process pursuant to which silica gel is conventionally produced (silicon oxide is hydrolyzed to hydrosol and then gelled by agglomeration to a gel, that is hydrogel).

Channel cross sections which are even narrower (capillaries) can be coated with an indicator layer directly according to the same sol-gel process. Such coating actions can take place by means of gluing the surfaces with a powder-like indicator dust. Both coating methods including information as to the suitable components and appropriate adhesive are disclosed in German Patent 1,037,725. The reagents mentioned in this patent for the detection of substances reacting therewith are also usable for the application in the detection apparatus according to the invention.

BRIEF DESCRIPTION OF THE DRAWINGS

The invention will now be described with reference to the drawings, wherein:

FIG. 1 is a plan view of an embodiment of a carrier of the apparatus according to the invention with the carrier having a plurality of channels;

FIG. 2 is a section view taken along line 2—2 of FIG. 1;

FIG. 3 is an end elevation view of the carrier of FIG. 1;

DESCRIPTION OF THE PREFERRED EMBODIMENTS OF THE INVENTION

Figure 5:
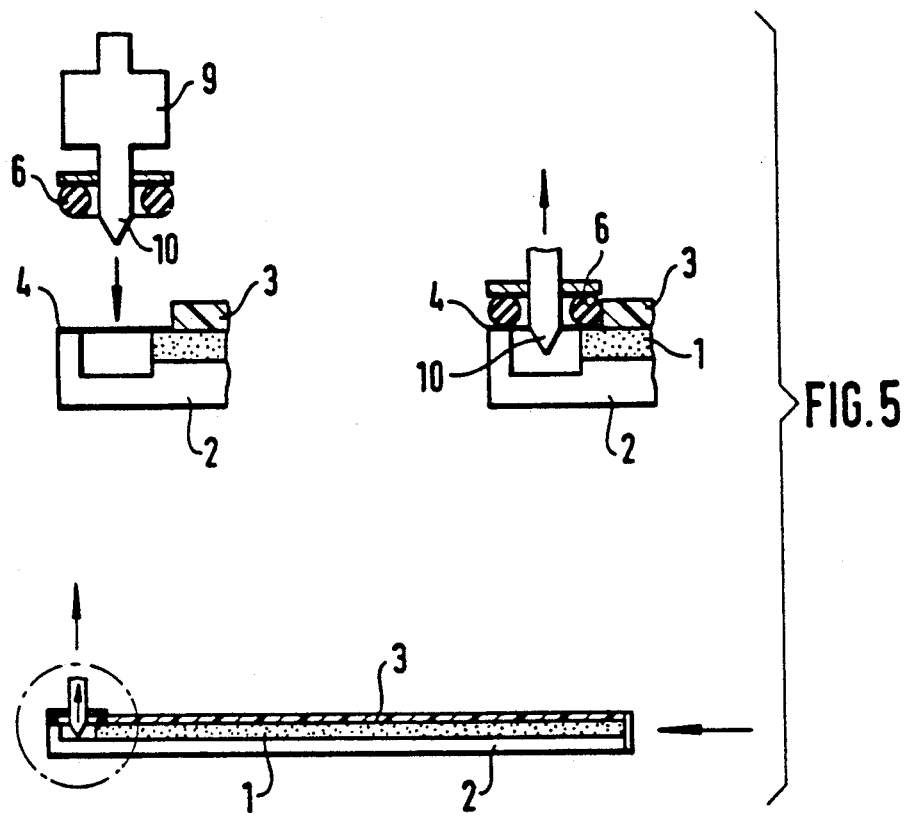
FIG. 5 is a sequence of views explaining the individual steps for establishing the pump connection with pertinent portions of the carrier being shown in cross section.

FIGS. 1 to 3 show a plate-shaped carrier 2 containing a plurality of channels 1. The inlet or suction openings of the channels 1 are closed off by a closure foil 4 before use. The closure foil 4 can be pulled off or be penetrated. Appropriate reagents are disposed in the channels 1 for the gas components to be detected.

A forward layer 5 for depositing moisture is connected ahead of the individual channels 1 at the inlet end. The channels 1 are covered on the upper side of the carrier by a cover plate 3.

In the embodiment shown, it is intended to bring the individual channels 1 sequentially into the active area of the opto-electronic scanning device explained with reference to FIG. 6. A pair of rubber-elastic transport rollers (7, 8) represent a transport device for the carrier 2 and effect the required displacement movement of this carrier 2.

Figure 4:
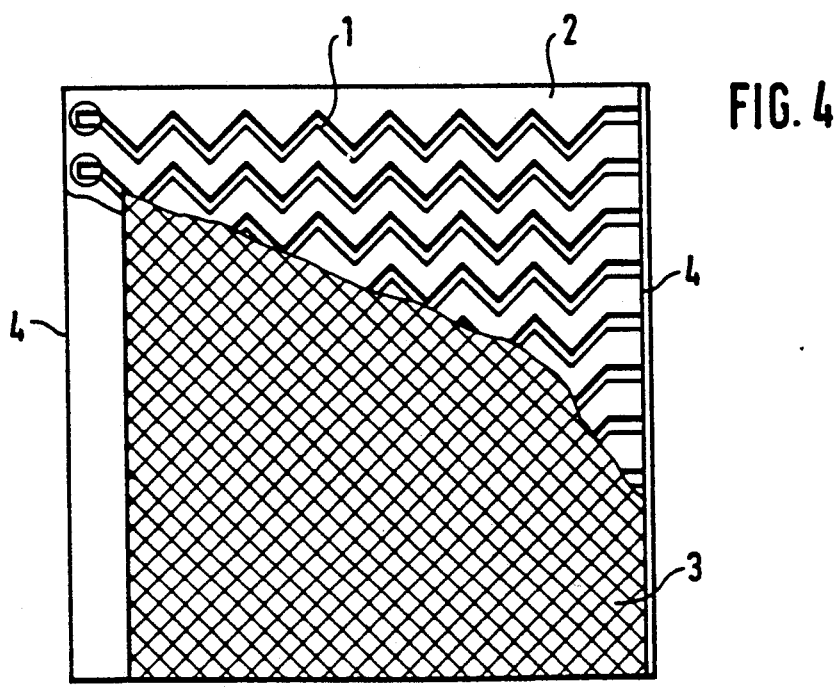
FIG. 4 is a plan view of an alternate embodiment of a carrier of the apparatus according to the invention with the carrier having a plurality of channels defining respective zigzag paths.

In the configuration of the carrier shown in FIG. 4, each of the individual channels 1 defines a zigzag path. The suction openings of the channels open at the upper side of the carrier 2 in this embodiment and, like the inlet openings of the channels, are covered with the removable closure foil 4.

FIG. 5 explains the operation when connecting the suction pump 9 which draws the gas mixture through the particular channel 1 monitored by the scanning device. A displaceable penetrating connection 10 is connected with the suction pump 9 and the penetrating connection 10 is sealed about its periphery by means of an elastic ring seal 6. When displacing the penetrating connection 10 forwardly, the closure foil 4 is penetrated and a connection to the suction pump 9 is established. This connection is sealed by the elastic sealing ring 6.

Figure 6:
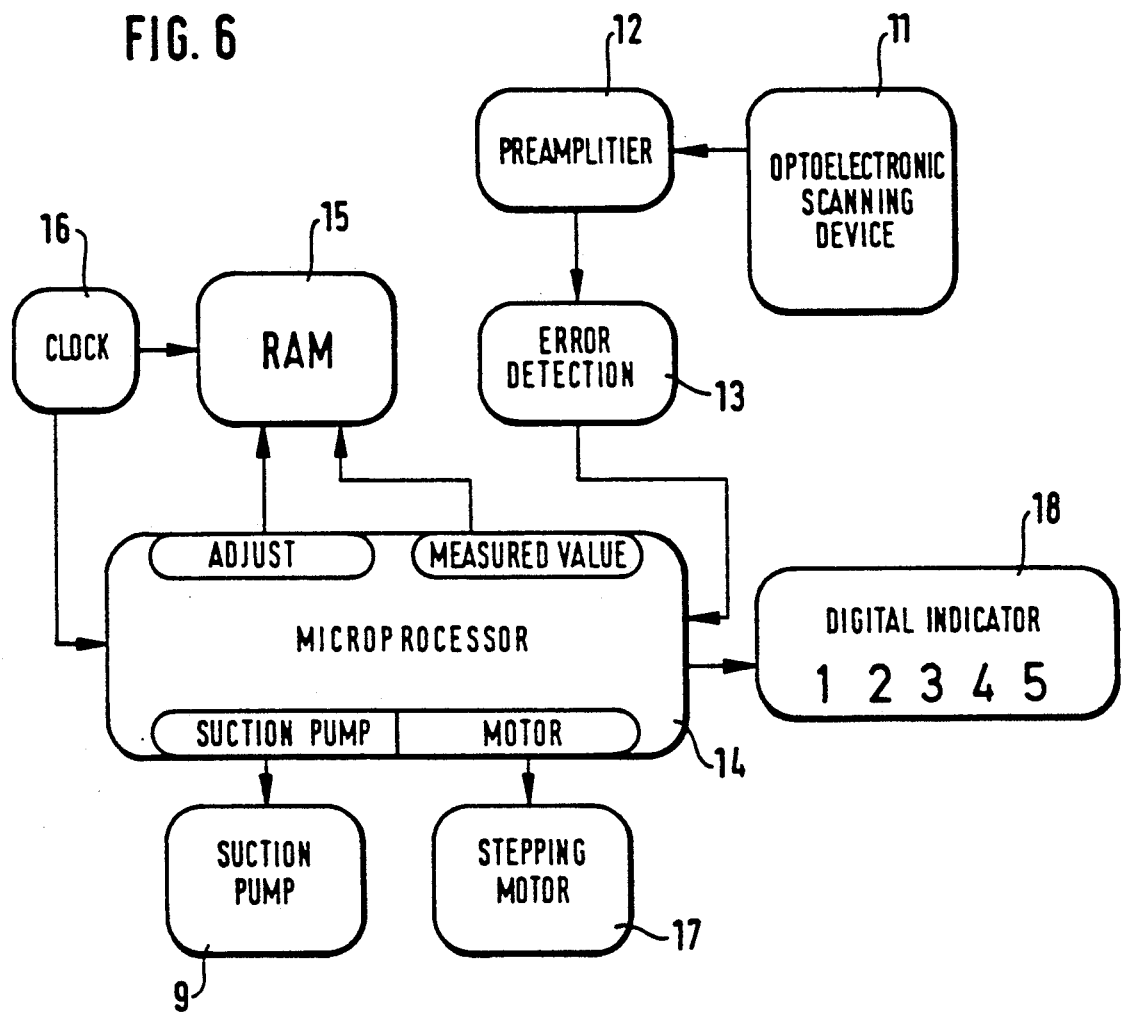
FIG. 6 is a block diagram of a measuring apparatus for use in combination with the carrier shown in FIGS. 1 to 5; and, FIG. 7 is a section view taken through a coated channel.

In the block diagram of FIG. 6, an opto-electronic scanning device 11 is shown which makes possible a scanning of the length of the colored layer in the individual channels.

Such scanning devices are known in different embodiments and can, for example, be configured with a LED-array as shown in German Patent 2,628,790.

The opto-electronic scanning device 11 detects a bar code via a bar-code reader with the bar code being disposed on the plate-shaped carrier 2 and assigned to channels 1. The type and number of the channels is coded into the bar code. Furthermore, a position sensor can be integrated into the opto-electronic scanning device by means of which it is assured that the particular channel to be measured or a plurality of channels which are to be measured are disposed in the correct position with respect to the scanning device.

The signal of the opto-electronic scanning device 11 is transmitted via a preamplifier 12 into an error detector 13 which examines the read-in information for correctness, that is, the signal is defined as a possible measured value.

The signals transmitted from the error detector 13 are processed in a microprocessor 14 as measured values, that is, they are compared with a predetermined threshold value and stored in a RAM (Random-Access-Memory) memory 15. A clock generator 16 controls the RAM memory 15 and the microprocessor 14.

The microprocessor 14 further controls the suction pump 9 as well as a stepper motor 17 pursuant to the data of the bar code on the carrier. The suction pump 9 is connected to the channel to be investigated and is switched on for a short time for generating the gas flow in the channel 1. After ending the measurement of a channel or several channels measured simultaneously, the step motor 17 is switched on and the plate-shaped carrier 2 is transported into the next measuring position by means of the elastic transport rollers (7, 8) shown in FIG. 2. When the measuring position is reached in the manner required, the pump connection is again established and the suction pump 9 is switched on. These operations are repeated until all channels of the carrier have been measured. The measuring result is then supplied as a digital indication by an indicating device 18.

The microprocessor can be preferably connected to a ROM (Read-Only-Memory) into which a plausibility model has been read and this plausibility model is compared to the stored measured values. For example, for unknown gas mixture compositions and based upon the data on the carrier, that is, the data contained on the readable bar code, it can be distinguished whether specific channel combinations such as the channels 2 and 3 are colored. In this case, the indication is made that strong acids must be present in the gas mixture if the channels 2 and 3 are generally sensitive to acids independently of their composition.

Figure 7:
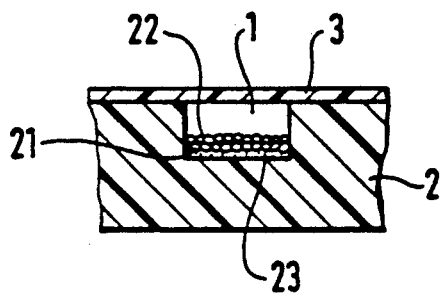

In the section view shown in FIG. 7, the channel 1 is provided with a layer of small glass beads 21 which is coated by the indicator 22 in accordance with the sol-gel process. The individual beads 21 are glued to the channel wall by an adhesive layer 23.

It is understood that the foregoing description is that of the preferred embodiments of the invention and that various changes and modifications may be made thereto without departing from the spirit and scope of the invention as defined in the appended claims.

What is claimed is:

1. An apparatus for measuring the concentration of the gaseous and/or vaporous components of a gas mixture, the apparatus comprising:

a carrier;

a plurality of through-flow channels extending over substantially the entire length or width of the carrier and being formed on said carrier so as to permit parallel flows of a gas mixture therethrough;

a substance disposed in said through-flow channels for reacting with any components to be measured to thereby define a reaction zone which can be visually monitored for changes therein;

said through-flow channels having respective longitudinal inlet ends for admitting a gas mixture and respective longitudinal outlet ends for permitting the gas mixture to pass out of said through-flow channels;

first removable closure means for closing off said inlet ends until removed preparatory for making a measurement of a gas mixture; and, second removable closure means for closing said outlet ends until removed preparatory for making a measurement of a gas mixture.

2. The apparatus of claim 1, each of said through-flow channels having a cross section in said reaction zone of less than 1 $mm^2$.

3. The apparatus of claim 2, said cross section being less than 10 $\mu m^2$.

4. The apparatus of claim 1, said plurality of through-flow being disposed so as to lie one next to the other; and, means for separately connecting said through-flow channels.

5. The apparatus of claim 1, said plurality of through-flow channels being formed on said carrier so as to define respective meandering paths.

6. The apparatus of claim 1, said carrier being a plate carrier; and, said through-flow channels being etched into said carrier.

7. The apparatus of claim 6, said carrier being made of glass.

8. The apparatus of claim 7, said carrier being made of ceramic.

9. The apparatus of claim 1, said carrier being a plate carrier; and, said through-flow channels being pressed into said carrier.

10. The apparatus of claim 9, said carrier being made of glass.

11. The apparatus of claim 1, said carrier being a plate carrier; and, said through-flow channels being cut into said carrier.

12. The apparatus of claim 11, said carrier being made of glass.

13. The apparatus of claim 1, said carrier including a carrier base and a surface coating applied to said base; and, said through-flow channels being formed between said surface coating and said base.

14. The apparatus of claim 1, said carrier including a carrier base and a cover plate covering said base; and, said through-flow channels being formed between said base and said cover plate.

15. The apparatus of claim 1, said through-flow channels being formed in said carrier; and, an advance layer disposed in each of said through-flow channels ahead of said reaction zone.

16. The apparatus of claim 1, wherein said carrier together with said substance is a throw-away article.

17. The apparatus of claim 1, said carrier being a plate carrier; each of said through-flows channels having a cavity formed in said carrier at said outlet end thereof; and, said second removable closure means being penetrable sealing means covering the respective cavities of said through-flow channels.

18. The apparatus of claim 17, further comprising displaceable suction pump means for penetrating said sealing means to establish a partial vacuum in a selected one of said cavities thereby causing a gas mixture to be drawn through the through-flow channel corresponding to said one cavity.

19. The apparatus of claim 1, each of said through-flow channels being provided with a layer of glass beads; and, said substance being coated on said glass beads.

20. An apparatus for measuring the concentration of the gaseous and/or vaporous components of a gas mixture, the apparatus comprising:
an opto-electronic scanning device;
a carrier;
a plurality of through-flow channels formed in said carrier for receiving the gas mixture to be tested;
substance means disposed in said through-flow channels for reacting with any components to be measured to thereby define respective reaction zones which can be visually monitored for changes therein;
said through-flow channels having respective first longitudinal inlet ends for admitting a gas mixture and respective second longitudinal outlet ends for permitting the gas mixture to pass out of said through-flow channels;
first removable closure means for closing off said inlet ends until removed preparatory for making a measurement of a gas mixture;
second removable closure means for closing said outlet ends until removed preparatory for making a measurement of a gas mixture; and,
indexing means for imparting a relative movement between said carrier and said scanning device so as to permit said reaction zones to be sequentially measured by said scanning device.

21. The apparatus of claim 20, each of said through-flow channels having a cross section in said reaction zone of less than 1 mm$^2$.

22. The apparatus of claim 20, said carrier being a plate carrier; each of said through-flow channels having a cavity formed in said carrier at the outlet end thereof; and, said second removable closure means being penetrable sealing means covering the respective cavities of said through-flow channels.

23. The apparatus of claim 22, further comprising displaceable suction pump means for penetrating said sealing means to establish a partial vacuum in a selected one of said cavities thereby causing a gas mixture to be drawn through the through-flow channel corresponding to said one cavity.

* * * * *

UNITED STATES PATENT AND TRADEMARK OFFICE
CERTIFICATE OF CORRECTION

PATENT NO. : 5,089,232
DATED : February 18, 1992
INVENTOR(S) : Wolfgang May

It is certified that error appears in the above-identified patent and that said Letters Patent is hereby corrected as shown below:

In column 4, line 45: between "or" and "penetrated", delete "be".

In column 6, line 36: between "through-flow" and "being", insert -- channels --.

In column 7, line 6: delete "through-flows" and substitute -- through-flow -- therefor.

Signed and Sealed this

Fourth Day of May, 1993

Attest:

MICHAEL K. KIRK

Attesting Officer    Acting Commissioner of Patents and Trademarks